(12) United States Patent
Xu

(10) Patent No.: US 9,164,069 B2
(45) Date of Patent: Oct. 20, 2015

(54) POTENTIOMETRIC TITRATION METHOD OF A MIXED ACID SOLUTION

(71) Applicant: Shenzhen China Star Optoelectronics Technology Co., Ltd., Shenzhen, Guangdong (CN)

(72) Inventor: Rui Xu, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 113 days.

(21) Appl. No.: 14/233,148

(22) PCT Filed: Nov. 22, 2013

(86) PCT No.: PCT/CN2013/087665
§ 371 (c)(1),
(2) Date: Jan. 15, 2014

(87) PCT Pub. No.: WO2015/070478
PCT Pub. Date: May 21, 2015

(65) Prior Publication Data
US 2015/0140675 A1  May 21, 2015

(30) Foreign Application Priority Data
Nov. 15, 2013 (CN) .......................... 2013 1 0576348

(51) Int. Cl.
*G01N 31/16* (2006.01)
*C09K 13/00* (2006.01)

(52) U.S. Cl.
CPC ............. *G01N 31/16* (2013.01); *C09K 13/00* (2013.01)

(58) Field of Classification Search
CPC ..................................................... G01N 31/16
USPC ....................... 436/100–102, 129, 150, 163
See application file for complete search history.

(56) References Cited

U.S. PATENT DOCUMENTS 2,597,702 A * 5/1952 Benning ....................... 558/204
3,133,787 A * 5/1964 Kelley, Jr. ...................... 422/15
(Continued)

FOREIGN PATENT DOCUMENTS

JP          07-286985      * 10/1995
KR            816657       *  3/2008

OTHER PUBLICATIONS

Moss M. L. et al, Analytical Chemistry 1948, 20, 784-788.*
(Continued)

*Primary Examiner* — Arlen Soderquist
(74) *Attorney, Agent, or Firm* — Andrew C. Cheng

(57) ABSTRACT

The present invention provides a potentiometric titration method of calculating a content of each acid in a mixed acid solution. The potentiometric titration method includes steps as follows. Step 1, an alkali-alcohol solution of a concentration in 0.1~0.2 mol/L is prepared and titrated with a basis reagent. Step 2, a first solvent and a second solvent are added into and stirred with a mixed acid solution consisted of nitric acid, phosphoric acid and acetic acid to form a mixed system, and the mixed system is titrated with the alkali-alcohol solution to obtain three equivalence points of the nitric acid, phosphoric acid and acetic acid in the mixed system. Step 3, a concentration of each acid in the mixed system is measured with the three equivalence points obtained in Step 2. According to the present invention, the content of each acid in the mixed acid solution can be rapidly and precisely measured.

8 Claims, 1 Drawing Sheet

(56) References Cited

U.S. PATENT DOCUMENTS

| | | | |
|---|---|---|---|
| 3,466,228 A * | 9/1969 | Trebes | 205/780 |
| 4,227,976 A * | 10/1980 | Menke | 205/81 |
| 6,494,961 B2 * | 12/2002 | Simpson | 134/3 |
| 7,622,305 B2 * | 11/2009 | Choi et al. | 436/163 |
| 8,945,934 B2 * | 2/2015 | Xu et al. | 436/100 |
| 2002/0072235 A1 * | 6/2002 | Haga et al. | 438/689 |
| 2002/0139397 A1 * | 10/2002 | Simpson | 134/15 |
| 2008/0063564 A1 * | 3/2008 | Choi et al. | 422/68.1 |
| 2014/0045271 A1 * | 2/2014 | Xu et al. | 436/100 |

OTHER PUBLICATIONS

Malmstadt, H. V. et al, Analytical Chemistry 1959, 31, 206-210.*
Das, M. N. et al, Analytical Chemistry 1959, 31, 233-237.*

* cited by examiner

POTENTIOMETRIC TITRATION METHOD OF A MIXED ACID SOLUTION

This application is a national stage application under 35 U.S.C. §371 of International Application Number PCT/CN2013/087665, filed Nov. 22, 2013, which claims priority from Chinese Patent Application Number 201310576348.0, filed Nov. 15, 2013.

FIELD OF THE INVENTION

The present invention relates to a titration method of a solution for use in an etching process, more particularly to a potentiometric titration method of a content of each acid in a mixed acid solution.

BACKGROUND OF THE INVENTION

The wet etching process is a core art of fabricating gate, source-drain and pixel electrode of a semiconductor device by using an acid etchant to pattern metal layers. In general, aluminum and molybdenum are often used as the metal layers to form the gate pattern, a wet etching process of the aluminum and molybdenum layers can use a variety of acids; however, a mixed acid such as a composition of phosphoric acid, nitric acid and acetic acid is the most popular etchant for use in the wet etching process to dissolve and redox the aluminum and molybdenum layers, so that the gate pattern can be obtained.

A mixed acid of an aluminum etchant is consisted of phosphoric acid (about 70~72%), nitric acid (about 1.8~2.0%) and acetic acid (about 9.5~10.5%), a reaction formula of each acid in the mixed acid is illustrated as follows:

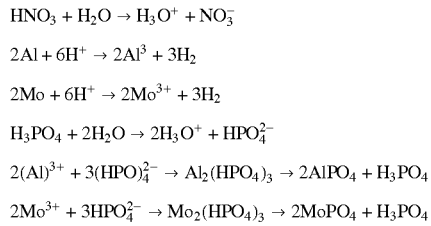

In the above reaction formulas, the nitric acid is as a role of providing $H_3O^+$ and etching alumina, the phosphoric acid provides phosphate to form a dissolvable complex with metal oxides, and the acetic acid can adhere on a surface of the reactant to reduce viscosity of the aluminum etchant so as to enhance wettability and adjust the etching rate. In the etching process, adjusting concentration of the nitric acid and the acetic acid is a key point of etching rate and pattern integrity.

Based on the acid-base theory, acidity of an acid or alkalinity of an alkali in solution is not only pertaining to the acid-base properties of themselves, but also related to a solvent of the solution. In aqueous solution, a difference of the ionization constant (pKa value) of the respective solutes therein is up to 5 so that the respective solutes can be measured by titration. For example, in a mixed acid solution consisted of nitric acid, phosphoric acid and acetic acid, the pKa of the nitric acid is −1.32, the first degree ionization constant ($pKa_1$) of the phosphoric acid is 1.96, concentrations of the nitric acid and phosphoric acid cannot be respectively measured by titration due to the leveling effect formed between the nitric acid and the phosphoric acid; similarly, and the pKa of the acetic acid is 4.73, the second degree ionization constant (pKa2) of the phosphoric acid is 7.12, concentrations of the acetic acid and phosphoric acid cannot be respectively measured by titration. In an appropriated non-aqueous solution, a difference of the ionization constant (pKa value) of the respective solutes therein is up about to 2~3 so that the respective solutes can be measured by titration. Therefore, an appropriated non-aqueous solvent is needed for use in titration of a mixed acid solution.

Due to high sensitivity, high accuracy, automation and continuous measurement, a potentiometric titration that determines a titration end point with a potential jump occurring in titration has been widely used. However, a conventional potentiometric titration of a mixed acid is mostly based on a two-steps method which is performed with a non-aqueous solvent. The conventional potentiometric titration includes: step 1, a content of a nitric acid in a mixed acid is titrated with tetrabutylammonium bromide as a titrant dissolved in ethanol solution and ethanol as a solvent, or KOH as a titrant dissolved in isopropanol solution and methanol as a solvent; step 2, contents of phosphoric acid and acetic acid are titrated with NaOH solution as a titrant and a saturated sodium chloride solution as a solvent. Two titration end points are sequentially occurred in the two-steps method, wherein the first titration end point is related to the nitric acid and the first hydrogen ion of the phosphoric acid, the second titration end point is related to the second hydrogen ion of the phosphoric acid and acetic acid, and then contents of the three acids in the mixed acid are obtained with automatic measurement. The conventional potentiometric titration which is performed with the two-steps method such as the above description has cumbersome and time-consuming process and a variety of titrants with solvents, so that the titration results are come with increased uncertain, reduced accuracy and worse reproducibility.

SUMMARY OF THE INVENTION

In order to obviate the above drawbacks, the present invention provides a novel potentiometric titration method of a mixed acid solution including steps as follows:

step 1, preparing an alkali-alcohol solution of a concentration in 0.1~0.2 mol/L, and titrating the concentration of the alkali-alcohol solution with a basis reagent by using an automatic titrator;

step 2, adding a first solvent and a second solvent into a mixed acid solution consisted of nitric acid, phosphoric acid and acetic acid, then stirring the first solvent, the second solvent and the mixed acid solution to form a mixed system, and titrating the mixed system with the alkali-alcohol solution titrated in the step 1 to obtain three equivalence points of the nitric acid, phosphoric acid and acetic acid in the mixed system by using the automatic titrator, wherein a volume ratio of the first solvent to the second solvent is 8~16:1, the first solvent is ethanol, and the second solvent is ethylene diamine or butylamine; and step 3, according to the principle of mass conservation, measuring a content of each acid in the mixed system with the three equivalence points obtained in the step 2.

In an embodiment, the step 2 further including: titrating the first solvent and the second solvent in the mixed acid solution with the alkali-alcohol solution titrated in the step 1 to obtain a background acid concentration equivalence point so as to eliminate an effect of the background acid concentration in measuring the content of the acetic acid.

In an embodiment, a total volume of the first solvent and the second solvent in a ratio of a mass of the mixed acid is 200~400 mL:1 g.

In an embodiment, an alkali in the alkali-alcohol solution is analytical pure potassium or sodium hydroxide, and a solvent in the alkali-alcohol solution is ethanol or ethylene glycol.

In an embodiment, the basis reagent is benzoate or potassium hydrogen phthalate.

According to the present invention, a titration buffer consisted of the first solvent and the second solvent is introduced in a titration of the mixed acid solution. An alkaline solvent such as ethylenediamine or butylamine allows a titration of a mixed acid solution performed in an alkaline environment so as to form a pronounced potential jump, reduce a recognition time of an electrode end point and enhance test efficiency of the titration; on the other hand, an increased amount of ethanol as a neutral solvent can reduce viscosity coefficient of the titration environment so as to increase transport and reaction rate of acid ions and alkaline ions in the mixed system and improve response efficiency of the titration. In the present invention, concentrations of the nitric acid, the phosphoric acid and the acetic acid can be rapidly and accurately titrated; simultaneously, a titration time can be greatly reduced, and efficiency and reproducibility of the titration can be enhanced. It is a great significance of adjusting an etch rate and forming a fine gate shape to control a concentration of each acid in the mixed acid solution used as an etchant, therefore, the present invention can be widely promoted in the TFT industry.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

Figure 1:
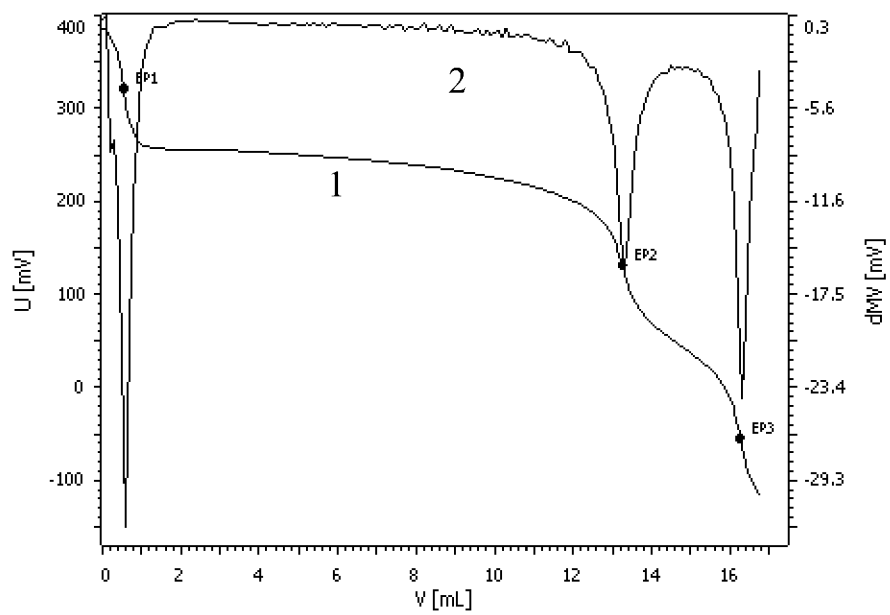
FIG. 1 illustrates potentiometric titration curves of a mixed acid in an alkaline environment according to Embodiment 1 of the present invention.

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

With a non-aqueous titration, an acid-base titration not reacted in aqueous phase can be performed so as to expand a titration scope thereof. The non-aqueous titration is based upon concept of the acid-base theory, and solvents in the non-aqueous titration have great influence on the strength of the acid-base.

The present invention provides a one-step titration method to titrate a concentration of each acid in a mixed acid with an alkali-alcohol solution as a titrant, a mixed solvent consisted of an amphoteric solvent and an alkaline solvent as a titration buffer. In the alkali-alcohol solution, an alcohol solvent can be ethanol or ethylene glycol. Principles of selecting the alcohol solvent include low cost, easy to get, high alkali solubility, fully miscible with a solvent for use in the mixed acid. In the amphoteric solvent, i.e. a first solvent according to the present invention, can be ethanol; and the alkaline solvent, i.e. a second solvent according to the present invention, can be ethylene diamine or butylamine. A titration buffer is consisted of the first solvent and the second solvent, an amount of the titration buffer is depended on an amount of titration sample, and a ratio between the titration buffer and the titration sample needs to meet certain conditions.

Embodiment 1

Embodiment 1 according to the present invention includes steps as follows.

Step 1, an alkali-ethylene glycol solution of a concentration in 0.1~0.2 mol/L is prepared, and the concentration of the alkali-ethylene glycol solution is titrated with a basis reagent by using an automatic titrator. In this embodiment, the alkali-ethylene glycol solution is a potassium hydroxide (KOH)-ethylene glycol solution prepared with analytical pure KOH.

In step 1, 65.9 g of KOH (analytical pure concentration greater than 85%) is accurately weighed by using an electronic balance, the KOH is dissolved with an appropriate amount of ethylene glycol to form the KOH-ethylene glycol solution of a concentration about 1 mol/L, the KOH-ethylene glycol solution is kept still and precipitated for 15 days, an appropriate amount of an upper clear liquid in the alkali-ethanol solution is extracted, the upper clear liquid is diluted with an appropriate amount of ethylene glycol to a preferred concentration about 0.1 mol/L, and an un-titrated KOH-ethylene glycol solution is obtained by performing a vacuum-filtrating process.

In this embodiment, the un-titrated KOH-ethylene glycol solution is titrated with benzoic acid (also potassium hydrogen phthalate known in the art) as the basis regent. In details, the benzoic acid is baked in an oven at 105° C. to have a constant weight, then the benzoic acid is cooled in a dryer at least for 1 hour, an appropriate weight amount of the benzoic acid as a solute is weighed (accuracy in 0.1 mg deviation) and added into an automatic potentiometric titrator. An appropriate amount of ethanol as a solvent is then added to dissolve the benzoic acid at room temperature and immerse the electrodes of the automatic potentiometric titrator. Then, the un-titrated KOH-ethylene glycol solution is respectively titrated with the benzoic-ethanol solution by using the automatic potentiometric titrator to obtain a first titration end point, and a concentration of the KOH-ethylene glycol solution is measured with the first titration end point. The above titration is parallel performed by three times, and an averaged concentration of the KOH-ethylene glycol solution is obtained. The specific titration results according to Step 1 in Embodiment 1 are shown in Table 1.

TABLE 1 titration results of the KOH-ethylene glycol solution

| titration | m/g | $V_{EP}$/mL | $U_{EP}$/mV | C/mol/L |
|---|---|---|---|---|
| 1 | 0.18191 | 13.3838 | −108.5 | 0.1113 |
| 2 | 0.19943 | 14.6462 | −112.8 | 0.1115 |
| 3 | 0.18441 | 13.5552 | −109.6 | 0.1114 |
| RSD/% | | | | 0.07 |

Remarks:
$V_{EP}$ represents a consumed volume of KOH-ethylene glycol at equivalence point;
$U_{EP}$ represents a potential value at equivalence point C represents a titrated concentration of the KOH-ethylene glycol solution.

According to Table 1, in this embodiment, an actual concentration of the KOH-ethylene glycol solution is 0.1114 mol/L.

Step 2, in this embodiment, a mixed acid is prepared with nitric acid, phosphoric acid and acetic acid all of known concentrations. In details, 4.0843 g of 70.76 wt % nitric acid, 124.5017 g of 85.69 wt % phosphoric acid and 14.989 g of 99.99 wt % acetic acid are weighed and mixed with water, so that 150.0950 g of a mixed acid solution is formed.

Then, 35.5 mL ($V_1$) of a first solvent (ethanol) and 4.5 mL ($V_2$) of a second solvent (ethylene diamine) are added into and stirred with 0.2 g of the mixed acid solution to form a mixed system, at this moment, a total volume of the first solvent and the second solvent in a ratio of a mass of the mixed acid is 200 mL:1 g. Then, the mixed system is titrated with the KOH-ethylene glycol solution titrated in the step 1 to obtain three equivalence points (EP1, EP2 and EP3) of the nitric acid, phosphoric acid and acetic acid in the mixed system by using the automatic titrator, and concentrations of the nitric acid, phosphoric acid and acetic acid are respectively measured. The above titration is parallel performed by three times, and averaged concentrations of the nitric acid, phosphoric acid and acetic acid are respectively obtained.

Additionally, due to the first solvent and the second solvent having certain acidity, the certain acidity of the first solvent and the second solvent can interfere with the titration of the acetic acid and increase the titration result thereof. Therefore, in a preferred embodiment, the certain acidity of a titration buffer which is consisted of the first solvent and the second solvent is titrated before the titration of the mixed system is performed, namely, a blank titration method is performed in order to eliminate an effect of the background acid concentration in measuring the content of the acetic acid. Specifically, after the mixed acid solution is prepared, the mixed acid solution is titrated with the KOH-ethylene glycol solution titrated in the step 1 to obtain a background acid concentration equivalence point (blank) so as to eliminate an effect of the background acid concentration in measuring the content of the acetic acid.

Step 3, according to the principle of mass conservation, a mass ratio of each acid in the mixed system is measured with the three equivalence points thereof obtained in the step 2 and following formulas.

$$m_{HNO3}\% = V_{EP1} \times C \times M_{HNO3}/m$$

$$M_{H3PO4}\% = (V_{EP2} - V_{EP1}) \times C \times M_{H3PO4}/m$$

$$m_{HAc}\% = (V_{EP3} - V_{EP2} - V_{blank}) \times C \times M_{HAc}/m$$

In the above formulas, C represents concentration of the KOH-ethylene glycol, and measurement unit of C is mol/L;

$V_{EP1}$ represents a consumed volume of the KOH-ethylene glycol solution at the first equivalence point of the first acid (the nitric acid) in the mixed system, and measurement unit of $V_{EP1}$ is L;

$V_{EP2}$ represents a consumed volume of the KOH-ethylene glycol solution at the second equivalence point of the second acid (the phosphoric acid) in the mixed system, and measurement unit of $V_{EP2}$ is L;

$V_{EP3}$ represents a consumed volume of the KOH-ethylene glycol solution at the third equivalence point of the third acid (the acetic acid) in the mixed system, and measurement unit of $V_{EP3}$ is L;

$V_{blank}$ represents a consumed volume of the KOH-ethylene glycol solution at the background acid concentration equivalence point of the background acid (the ethanol) in the mixed system, and measurement unit of $V_{blank}$ is L;

m represents a weighed mass of the mixed acid, and measurement unit of m is g;

M represents a molar mass of each acid.

The specific titration results according to Step 2 in Embodiment 1 are shown in Table 2 and Table 3.

TABLE 2 the consumed volume of the KOH-ethylene glycol solution and the potential value of each equivalence point of each acid in the mixed system

| | m/g | $V_{EP1}$/mL | $U_{EP1}$/mV | $V_{EP2}$/mL | $U_{EP2}$/mV | $V_{EP3}$/mL | $U_{EP3}$/mV | $V_{blank}$/mL | $U_{blank}$/mV |
|---|---|---|---|---|---|---|---|---|---|
| 1 | 0.1956 | 0.5452 | 321.7 | 13.2441 | 130.8 | 16.2578 | −54.3 | 0.1061 | −49.8 |
| 2 | 0.2006 | 0.5671 | 332.7 | 13.6572 | 129.5 | 16.7338 | −50.8 | 0.1028 | −48.5 |
| 3 | 0.2090 | 0.5857 | 330.6 | 14.2193 | 130.3 | 17.4419 | −51.4 | 0.1087 | −50.3 |

TABLE 3 the mass ratio concentration of each acid in the mixed system

| | $m_{HNO3}$% | $m_{H3PO4}$% | $m_{HAc}$% |
|---|---|---|---|
| Preparation concentration | 1.93 | 71.12 | 9.98 |
| Titration concentration 1 | 1.96 | 70.88 | 9.94 |
| Titration concentration 2 | 1.98 | 71.24 | 9.91 |
| Titration concentration 3 | 1.97 | 71.22 | 9.96 |
| Averaged concentration | 1.97 | 71.12 | 9.93 |
| Deviation % | 2.07 | −0.01 | −0.45 |
| RSD/% | 0.41 | 0.23 | 0.21 |

FIG. 1 illustrates potentiometric titration curves according to the titration results as shown in Table 2 and Table 3. Please refer to FIG. 1, curve 1 is a titration curve, curve 2 is a data derivation (d) of the curve 1, and the curve 2 can assist accurately identify potential jumps (i.e. the equivalence point of the titration) EP1, EP2, EP3 on the curve 1. As shown in FIG. 1, three potential jumps are clearly visible on the curve 1, and the curve 2 clearly indicates three equivalence points EP1, EP2, EP3 of the titration on the curve 1. The curve 2 is relatively smooth and stable between two equivalence points in the titrating process, and becomes sharp to clearly indicate a potential value of each equivalence point on the curve 1.

As apparent from Table 2, Table 3 and FIG. 1, firstly, each acid in the mixed acid can be titrated with the one-step titration method according to the present invention, and the relative standard deviation (RSD %) of the concentration of each acid is less than 1%, so that the experimental data according to this embodiment are credible, stable and feasible. Secondly, a deviation between the titrated concentrations and actual concentrations of the nitric acid, phosphoric acid and acetic acid is less than ±3%, so that the titration method according to this embodiment is accurate and reliable.

In order to describe effects from a neutral titration buffer to a concentration of each acid in a mixed acid and titration time, a control experiment is carried out. In the control experiment, the neutral titration buffer is consisted of ethanol as a first solvent and 1,2-propanediol as a second solvent.

As the description of Step 1 in Embodiment 1, a KOH-ethanol solution is prepared, and an actual concentration of the KOH-ethanol is 0.1108 mol/L. Then, 20 mL of a first solvent (ethanol) and 20 mL of a second solvent (1,2-propanediol) are added into and stirred with 0.2 g of the mixed acid solution prepared as Step 2 in Embodiment 1 to form a mixed system, wherein a volume ratio of the first solvent (ethanol) to the second solvent (1,2-propanediol) is 1:1, and a mass of the mixed acid in a ratio of a total volume of the first solvent and the second solvent is 1 g:200 mL. Then, the mixed system is titrated with the KOH-ethanol solution to obtain three equivalence points (EP1, EP2 and EP3) of the nitric acid, phosphoric acid and acetic acid in the mixed system by using the automatic titrator, and concentrations of the nitric acid, phosphoric acid and acetic acid are respectively measured. The above titration is parallel performed by three times, and averaged concentrations of the nitric acid, phosphoric acid and acetic acid are respectively obtained.

The specific titration results and titration time according to the control experiment are shown in Table 4 and Table 5.

TABLE 4 the consumed volume of the KOH-ethylene solution, the potential value and the titration time at each equivalence point of each acid in the mixed system

| | m/g | $V_{EP1}$/mL | $U_{EP1}$/mV | $V_{EP2}$/mL | $U_{EP2}$/mV | $V_{EP3}$/mL | $U_{EP3}$/mV | Titration time of the control experiment/s | Titration time of Embodiment 1 t/s |
|---|---|---|---|---|---|---|---|---|---|
| 1 | 0.2051 | 0.5752 | 312.6 | 13.9304 | 113.2 | 17.1107 | −47.8 | 1063 | 824 |
| 2 | 0.2076 | 0.5882 | 302.4 | 14.0842 | 114.7 | 17.2818 | −17.6 | 1071 | 956 |
| 3 | 0.2013 | 0.5619 | 319.0 | 13.6013 | 120.6 | 16.7093 | −45.8 | 1035 | 966 |

TABLE 5 the mass ratio concentration of each acid in the mixed system

| | $m_{HNO3}$ % | $m_{H3PO4}$ % | $m_{HAc}$ % |
|---|---|---|---|
| Preparation concentration | 1.93 | 71.12 | 9.98 |
| Titration concentration 1 | 1.96 | 70.70 | 10.31 |
| Titration concentration 2 | 1.98 | 70.59 | 10.24 |
| Titration concentration 3 | 1.95 | 70.33 | 10.26 |
| Averaged concentration | 1.96 | 70.54 | 10.27 |
| Deviation/% | 1.64 | −0.82 | 2.91 |
| RSD/% | 0.60 | 0.22 | 0.27 |

Figure 2:
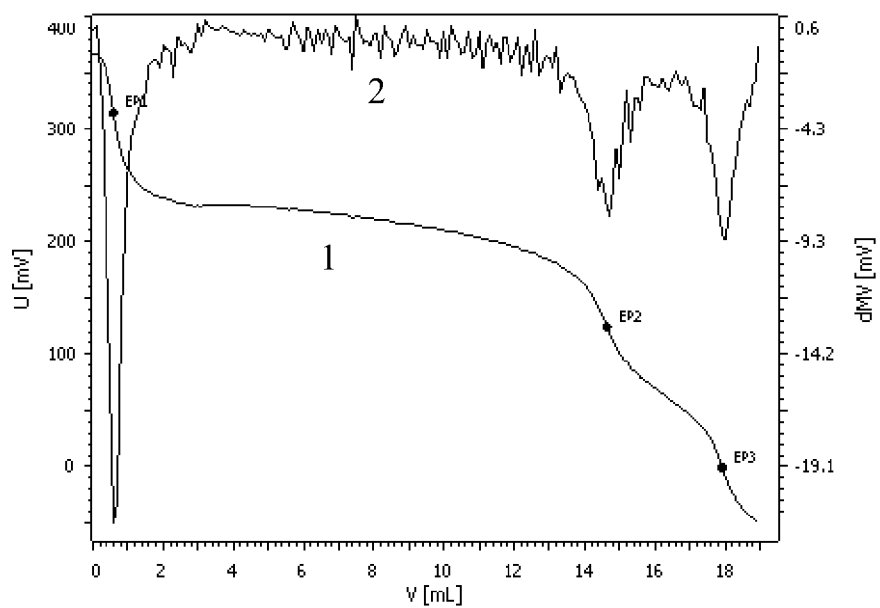
FIG. 2 illustrates potentiometric titration curves of a mixed acid according to a control experiment and Embodiment 1 of the present invention.

FIG. 2 illustrates potentiometric titration curves according to the titration results as shown in Table 4 and Table 5. Please refer to FIG. 2, curve 1 is a titration curve, curve 2 is a data derivation of the curve 1, and the curve 2 can assist identify potential jumps (i.e. the equivalence point of the titration) EP1, EP2, EP3 on the curve 1. However, the curve 2 is jagged between two equivalence points in the titrating process, so that the curve 2 is not conducive to accurately determine each equivalence point on the curve 1.

As apparent from Table 4, Table 5 and FIG. 2, firstly, although the relative standard deviation (RSD %) of the concentration of each acid in the neutral environment such as the control experiment can be less than 1%, a deviation between the titration concentration and the preparation concentration of the acetic acid according to the control experiment is about 3%, the deviation represents that the certain acidity of the first solvent (ethanol) and the second solvent (1,2-propandiol) interferes with the titration of the acetic acid and increase the titration result thereof. Secondly, in comparison of FIG. 1 and FIG. 2, it is obvious that the curve 2 in FIG. 1 is smoother than the curve 2 in FIG. 2, and an alkaline environment such as Embodiment 1 is conducive to accurately determine the titration end points. Meanwhile, the titration time of each acid in alkaline environment is shorter than the titration time of each acid in neutral environment about 140 s, so that the potential jump of each acid is more pronounced, the recognition time of the electrode end point is reduced, and the test efficiency of the titration is enhanced.

Embodiment 2

In this embodiment, a KOH-ethylene glycol solution is prepared as the description of Step 1 in Embodiment 1. Then, 75.3 mL ($V_1$) of a first solvent (ethanol) and 4.7 mL ($V_2$) of a second solvent (ethylene diamine) are added into and stirred with 0.2 g of the mixed acid solution prepared as Step 2 in Embodiment 1 to form a mixed system, wherein a mass of the mixed acid in a ratio of a total volume of the first solvent and the second solvent is 1 g:400 mL. Then, the mixed system is titrated with the KOH-ethylene glycol solution to obtain three equivalence points (EP1, EP2 and EP3) of the nitric acid, phosphoric acid and acetic acid in the mixed system by using the automatic titrator, and concentrations of the nitric acid, phosphoric acid and acetic acid are respectively measured. The above titration is parallel performed by three times, and averaged concentrations of the nitric acid, phosphoric acid and acetic acid are respectively obtained.

The specific titration results and titration time according to Embodiment 2 are shown in Table 6 and Table 7.

TABLE 6 the consumed volume of the KOH-ethylene glycol solution, the potential value and the titration time at each equivalence point of each acid in the mixed system

| | m/g | $V_{EP1}$/mL | $U_{EP1}$/mV | $V_{EP2}$/mL | $U_{EP2}$/mV | $V_{EP3}$/mL | $U_{EP3}$/mV | $V_{blank}$/mL | $U_{blank}$/mV |
|---|---|---|---|---|---|---|---|---|---|
| 1 | 0.1993 | 0.5502 | 329.6 | 13.5346 | 129.8 | 16.6953 | −53.9 | 0.2072 | −51.2 |
| 2 | 0.1966 | 0.5470 | 330.6 | 13.3494 | 128.9 | 16.4744 | −51.2 | 0.2054 | −49.5 |
| 3 | 0.2058 | 0.5804 | 328 | 13.9701 | 132.9 | 17.2264 | −51.9 | 0.2107 | −52.7 |

TABLE 7 the mass ratio concentration of each acid in the mixed system

|  | $m_{HNO_3}$ % | $m_{H_3PO_4}$ % | $m_{HAc}$ % |
|---|---|---|---|
| Preparation concentration | 1.93 | 71.12 | 9.98 |
| Titration concentration 1 | 1.94 | 71.13 | 9.91 |
| Titration concentration 2 | 1.95 | 71.09 | 9.93 |
| Titration concentration 3 | 1.98 | 71.03 | 9.89 |
| Averaged concentration | 1.96 | 71.08 | 9.91 |
| Deviation/% | 1.37 | −0.05 | −0.73 |
| RSD/% | 0.88 | 0.06 | 0.14 |

Embodiment 3

In this embodiment, butylamine is selected as a second solvent, 75.3 mL (V1) of a first solvent (ethanol) and 4.7 mL (V2) of a second solvent (butylamine) are added into and stirred with 0.2 g of the mixed acid solution prepared as Step 2 in Embodiment 1 to form a mixed system, wherein a volume ratio of the first solvent (ethanol) to the second solvent (butylamine) is 16:1, and a mass of the mixed acid in a ratio of a total volume of the first solvent and the second solvent is 1 g:400 mL. Then, the mixed system is titrated with the KOH-ethylene glycol solution to obtain three equivalence points (EP1, EP2 and EP3) of the nitric acid, phosphoric acid and acetic acid in the mixed system by using the automatic titrator, and concentrations of the nitric acid, phosphoric acid and acetic acid are respectively measured. The above titration is parallel performed by three times, and averaged concentrations of the nitric acid, phosphoric acid and acetic acid are respectively obtained.

The specific titration results and titration time according to Embodiment 3 are shown in Table 8 and Table 9.

TABLE 8 the consumed volume of the KOH-ethylene glycol solution, the potential value and the titration time at each equivalence point of each acid in the mixed system

|  | m/g | $V_{EP1}$/mL | $U_{EP1}$/mV | $V_{EP2}$/mL | $U_{EP2}$/mV | $V_{EP3}$/mL | $U_{EP3}$/mV | $V_{blank}$/mL | $U_{blank}$/mV |
|---|---|---|---|---|---|---|---|---|---|
| 1 | 0.2040 | 0.5711 | 325.1 | 13.8395 | 130 | 17.0527 | −50 | 0.1948 | −54.1 |
| 2 | 0.2100 | 0.5918 | 322.8 | 14.2945 | 124.6 | 17.5918 | −53.1 | 0.2012 | −52.9 |
| 3 | 0.1929 | 0.5486 | 321 | 13.0962 | 124.7 | 16.1593 | −51.1 | 0.1995 | −53.4 |

TABLE 9 the mass ratio concentration of each acid in the mixed system

|  | $m_{HNO_3}$ % | $m_{H_3PO_4}$ % | $m_{HAc}$ % |
|---|---|---|---|
| Preparation concentration | 1.93 | 71.12 | 9.98 |
| Titration concentration 1 | 1.97 | 71.02 | 9.89 |
| Titration concentration 2 | 1.98 | 71.25 | 9.86 |
| Titration concentration 3 | 2.00 | 71.01 | 9.92 |
| Averaged concentration | 1.98 | 71.10 | 9.89 |
| Deviation/% | 2.58 | −0.03 | −0.90 |
| RSD/% | 0.64 | 0.16 | 0.27 |

Embodiment 4

In this embodiment, butylamine is selected as a second solvent, 35.5 mL (V1) of a first solvent (ethanol) and 4.5 mL (V2) of a second solvent (butylamine) are added into and stirred with 0.2 g of the mixed acid solution prepared as Step 2 in Embodiment 1 to form a mixed system, wherein a volume ratio of the first solvent (ethanol) to the second solvent (butylamine) is 8:1, and a mass of the mixed acid in a ratio of a total volume of the first solvent and the second solvent is 1 g:200 mL. Then, the mixed system is titrated with the KOH-ethylene glycol solution to obtain three equivalence points (EP1, EP2 and EP3) of the nitric acid, phosphoric acid and acetic acid in the mixed system by using the automatic titrator, and concentrations of the nitric acid, phosphoric acid and acetic acid are respectively measured. The above titration is parallel performed by three times, and averaged concentrations of the nitric acid, phosphoric acid and acetic acid are respectively obtained.

The specific titration results and titration time according to Embodiment 4 are shown in Table 10 and Table 11.

TABLE 10 the consumed volume of the KOH-ethylene glycol solution, the potential value and the titration time at each equivalence point of each acid in the mixed system

| | m/g | $V_{EP1}$/mL | $U_{EP1}$/mV | $V_{EP2}$/mL | $U_{EP2}$/mV | $V_{EP3}$/mL | $U_{EP3}$/mV | $V_{blank}$/mL | $U_{blank}$/mV |
|---|---|---|---|---|---|---|---|---|---|
| 1 | 0.1988 | 0.5609 | 319   | 13.4734 | 123.1 | 16.5336 | −55.4 | 0.1084 | −49.7 |
| 2 | 0.2085 | 0.5816 | 320.2 | 14.1465 | 125.2 | 17.3664 | −55.3 | 0.1191 | −53.2 |
| 3 | 0.1946 | 0.5501 | 315.7 | 13.1826 | 110.7 | 16.1971 | −72.2 | 0.1205 | −51.8 |

TABLE 11 the mass ratio concentration of each acid in the mixed system

| | $m_{HNO3}$ % | $m_{H3PO4}$ % | $m_{HAc}$ % |
|---|---|---|---|
| Preparation concentration | 1.93 | 71.12 | 9.98 |
| Titration concentration 1 | 1.98 | 70.89 | 9.92 |
| Titration concentration 2 | 1.96 | 71.03 | 9.94 |
| Titration concentration 3 | 1.98 | 70.87 | 9.94 |
| Averaged concentration | 1.97 | 70.93 | 9.93 |
| Deviation/% | 2.27 | −0.26 | −0.45 |
| RSD/% | 0.58 | 0.10 | 0.09 |

As the description of Embodiment 1~4, the present invention provides a one-step titration method to titrate a concentration of each acid in a mixed acid, and the one-step titration method is more particularly suitable for use in titrating concentrations of a mixed acid solution as an aluminum etchant. Each acid in the mixed acid solution can be titrated with the one-step titration method according to each embodiment of the present invention, and the relative standard deviation (RSD %) of the concentration of each acid is less than 1%, so that the experimental data according to the embodiments are credible, stable and feasible. Moreover, a deviation between the titrated concentrations and actual concentrations of the nitric acid, phosphoric acid and acetic acid is less than ±3%, so that the titration method according to this embodiment is accurate and reliable.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A potentiometric titration method of a mixed acid solution, comprising steps as follows:
    step 1, preparing an alkali-alcohol solution of a concentration in 0.1~0.2 mol/L, and titrating the concentration of the alkali-alcohol solution with a basis reagent by using an automatic titrator;
    step 2, adding a first solvent and a second solvent into a mixed acid solution consisted of nitric acid, phosphoric acid and acetic acid, then stirring the first solvent, the second solvent and the mixed acid solution to form a mixed system, and titrating the mixed system with the alkali-alcohol solution titrated in the step 1 to obtain three equivalence points of the nitric acid, phosphoric acid and acetic acid in the mixed system by using the automatic titrator, wherein a volume ratio of the first solvent to the second solvent is 8~16:1, the first solvent is ethanol, and the second solvent is ethylene diamine or butylamine; and
    step 3, according to the principle of mass conservation, measuring a content of each acid in the mixed system with the three equivalence points obtained in the step 2.

2. The potentiometric titration method according to claim 1, the step 2 further comprising: titrating the first solvent and the second solvent in the mixed acid solution with the alkali-alcohol solution titrated in the step 1 to obtain a background acid concentration equivalence point so as to eliminate an effect of the background acid concentration in measuring the content of the acetic acid.

3. The potentiometric titration method according to claim 1, wherein a total volume of the first solvent and the second solvent in a ratio of a mass of the mixed acid is 200~400 mL:1 g.

4. The potentiometric titration method according to claim 1, wherein an alkali in the alkali-alcohol solution is analytical pure potassium or sodium hydroxide, and a solvent in the alkali-alcohol solution is ethanol or ethylene glycol.

5. The potentiometric titration method according to claim 1, wherein the basis reagent is benzoic acid or potassium hydrogen phthalate.

6. A potentiometric titration method of a mixed acid solution, comprising steps as follows:
    step 1, preparing an alkali-alcohol solution of a concentration in 0.1~0.2 mol/L, and titrating the concentration of the alkali-alcohol solution with a basis reagent by using an automatic titrator;
    step 2, adding a first solvent and a second solvent into a mixed acid solution consisted of nitric acid, phosphoric acid and acetic acid, then stirring the first solvent, the second solvent and the mixed acid solution to form a mixed system, then titrating the mixed system with the alkali-alcohol solution titrated in the step 1 to obtain three equivalence points of the nitric acid, phosphoric acid and acetic acid in the mixed system by using the automatic titrator, and titrating the first solvent and the second solvent in the mixed acid solution with the alkali-alcohol solution titrated in the step 1 to obtain a background acid concentration equivalence point so as to eliminate an effect of the background acid concentration in measuring the concentration of the acetic acid, wherein a volume ratio of the first solvent to the second solvent is 8~16:1, the first solvent is ethanol, the second solvent is ethylene diamine or butylamine, and a total volume of the first solvent and the second solvent in a ratio of a mass of the mixed acid is 200~400 mL:1 g; and
    step 3, according to the principle of mass conservation, measuring a content of each acid in the mixed system with the three equivalence points obtained in the step 2.

7. The potentiometric titration method according to claim 6, wherein an alkali in the alkali-alcohol solution is analytical pure potassium or sodium hydroxide, and a solvent in the alkali-alcohol solution is ethanol or ethylene glycol.

8. The potentiometric titration method according to claim 6, wherein the basis reagent is benzoate or potassium hydrogen phthalate.

* * * * *